US005147380A

United States Patent [19]

Hernandez et al.

[11] Patent Number: 5,147,380

[45] Date of Patent: Sep. 15, 1992

[54] BIOPSY FORCEPS DEVICE HAVING IMPROVED LOCKING MEANS

[75] Inventors: Ernesto Hernandez, Miami; James A. Rigsby, North Miami Beach, both of Fla.

[73] Assignee: Cordis Corporation, Miami Lakes, Fla.

[21] Appl. No.: 770,606

[22] Filed: Oct. 3, 1991

[51] Int. Cl.[5] .............................................. A61B 10/00

[52] U.S. Cl. ...................................... 606/207; 128/751

[58] Field of Search ............................... 128/751, 749; 606/205-208

[56] References Cited

U.S. PATENT DOCUMENTS

| | | | |
|---|---|---|---|
| 4,318,313 | 3/1982 | Tartaglia | 606/207 |
| 4,644,651 | 2/1987 | Jacobsen | 128/751 |
| 4,815,476 | 3/1989 | Clossick | 606/207 |

FOREIGN PATENT DOCUMENTS

| | | | |
|---|---|---|---|
| 0752676 | 9/1933 | France | 606/207 |
| 2091624 | 8/1982 | United Kingdom | 606/205 |

*Primary Examiner*—Max Hindenburg
*Attorney, Agent, or Firm*—Tarolli, Sundheim & Covell

[57] ABSTRACT

A biopsy forceps device is presented herein having improved locking means for locking the forceps in a closed condition. This includes an elongated flexible hollow body portion having a lumen extending therethrough and having a proximal end coupled to a handle and a distal end coupled to a forceps assembly and which includes a pair of forceps. A control wire extends through the lumen in the hollow body portion and is coupled at its proximal end to the handle and at its distal end it is coupled to the forceps assembly. A trigger is connected to the proximal end of the control wire with the trigger being slidably mounted to the handle for slidable movement relative thereto between a rear position, at which the forceps are closed, and a forward position, at which the forceps are open. A releasable locking mechanism serves to normally block forward slidable movement of the trigger from its rear position toward its forward position to thereby prevent the forceps from being actuated to the open condition. The locking mechanism may be released with a release means which moves the locking means transversely of the direction of slidable movement of the trigger to thereby unblock such forward movement and thereby permit the trigger to actuate the forceps to the open condition.

8 Claims, 2 Drawing Sheets

10
12
14
16
18
20
22
24
30
32
34
36
38
40
42
46
48
60
62
64
66
68
70
80
82
100
102
110
112
120
122
124
130
134
136

100
112
130
108
102
104
36
46
106
110
22
80
82
20
70
66
64

BIOPSY FORCEPS DEVICE HAVING IMPROVED LOCKING MEANS

FIELD OF THE INVENTION

The present invention relates to biopsy forceps and, more particularly, to an improved biopsy forceps device having a handle assembly including improved locking means for locking the forceps in a closed position.

DESCRIPTION OF THE PRIOR ART

Biopsy forceps are known in the art and are in wide use for purposes of obtaining a tissue sample. One example of the prior art takes the form of the U.S. Pat. No. to J. P. Clossick, 4,815,476, assigned to the same assignee as the present invention. Such a forceps device includes a handle assembly slidably mounting a trigger member thereon and an elongated coil spring guide connected to the handle assembly at the proximal end of the guide. A pair of forceps are mounted to the distal end of the guide and a stylet-control wire received within the lumen of the guide is connected at its proximal end to the trigger and at its distal end to the pair of forceps.

A guide sheath may be introduced into a patient's body vessel, such as an artery, and the distal end of the forceps device is introduced into the sheath and guided to the site of interest. The handle assembly remains outside of the patient's body allowing the attending physician to operate the trigger. Forward movement of the trigger causes the stylet-control wire to move the forceps to an open position and rearward movement of the trigger causes the pair of forceps to move to a closed position to capture a tissue sample therebetween. The forceps device is then removed from the guide sheath so that the captured tissue sample may be examined.

It is desirable that the forceps remain closed while the captured tissue is being removed from the body vessel. If the forceps open during the removal process, the tissue sample may be lost within the patient's artery. Consequently, there is a need to provide such a forceps device having locking means for locking the forceps in a closed position to prevent loss of a captured tissue sample during the process of removing the sample from the body vessel.

A biopsy forceps device having a locking handle mechanism to achieve the foregoing is disclosed in the Clossick patent described hereinabove However, that device includes a locking hub assembly coupled between the handle and the proximal end of the stylet control wire. This includes a locking hub and locking means for locking the control wire in an axial position relative to the elongated coil spring guide upon rotation of the locking hub. In practice, it normally takes two hands to achieve this function. One hand must grasp the handle, while the other hand grasps the locking hub in order to rotate it about its axis of rotation to either lock or unlock the mechanism. It would be desirable if such a locking function could be accomplished with one hand only.

The handle assembly employed in the Clossick patent discussed above is sometimes referred to as a syringe-type handle in that it includes a figure eight double finger trigger slidably mounted on the handle portion. The handle portion has a thumb ring at one end thereof. This requires the attending physician to put his thumb in the thumb ring and grasp the trigger with two fingers to achieve slidable movement of the figure-eight trigger relative to the thumb ring when actuating the forceps between open and closed positions. The handle is grasped by a physician while attempting to remove captured tissue from a body vessel and has, in practice, been found somewhat uncomfortable to many physicians requiring modifications to the handle, such as a flexible coupling permitting angular pivotal movement of the handle during such operation. It would be desirable if a more ergonomic biopsy forceps handle be provided which would be more comfortable to the attending physician. A more comfortable handle, for example, might take the form of a sword-style handle which is shaped to fit the palm of a physician's hand and which includes a finger grip area contoured to receive the physician's fingers. Such a sword-like handle would be more comfortable for the physician and either hand can be employed in using the handle. Such a handle would be easier to grip and, hence, its ability to provide torque is greater than that known heretofore.

SUMMARY OF THE INVENTION

In accordance with the present invention, there is provided an improved biopsy forceps device having improved locking means for locking the forceps in a closed condition. Accordingly, there is provided an elongated flexible hollow body portion having a lumen extending therethrough and having a proximal end coupled to the handle assembly and a distal end coupled to a forceps assembly and which includes a pair of forceps. A control wire extends through the lumen in the hollow body portion and is coupled at its proximal end to the handle portion and at its distal end it is coupled to the forceps assembly. A trigger is connected to the proximal end of the control wire with the trigger being slidably mounted to the handle assembly for slidable movement relative thereto between a rear position, at which the forceps are closed, and a forward position, at which the forceps are open. A releasable locking mechanism serves to normally block forward slidable movement of the trigger from its rear position toward its forward position to thereby prevent the forceps from being actuated to the open condition. The locking mechanism may be released with a release means which moves the locking mechanism transversely of the direction of slidable movement of the trigger to such forward movement and thereby permit the trigger to actuate the forceps to the open condition.

In accordance with a still further aspect of the present invention, the handle assembly takes the form of a sword-like handle with the trigger being slidably mounted thereto so that it may be easily operated as with an operator's thumb for releasing the locking mechanism and permitting the trigger to actuate the forceps to an open condition. Both the locking-unlocking operation and the actuation of the forceps between open and closed conditions can be accomplished with one hand.

BRIEF DESCRIPTION OF THE DRAWINGS

The foregoing and other objects of the invention will become more readily apparent from the following description of the preferred embodiment of the invention as taken in conjunction with the accompanying drawings which are a part hereof and wherein.

DESCRIPTION OF THE PREFERRED EMBODIMENT

Figures 1, 2:
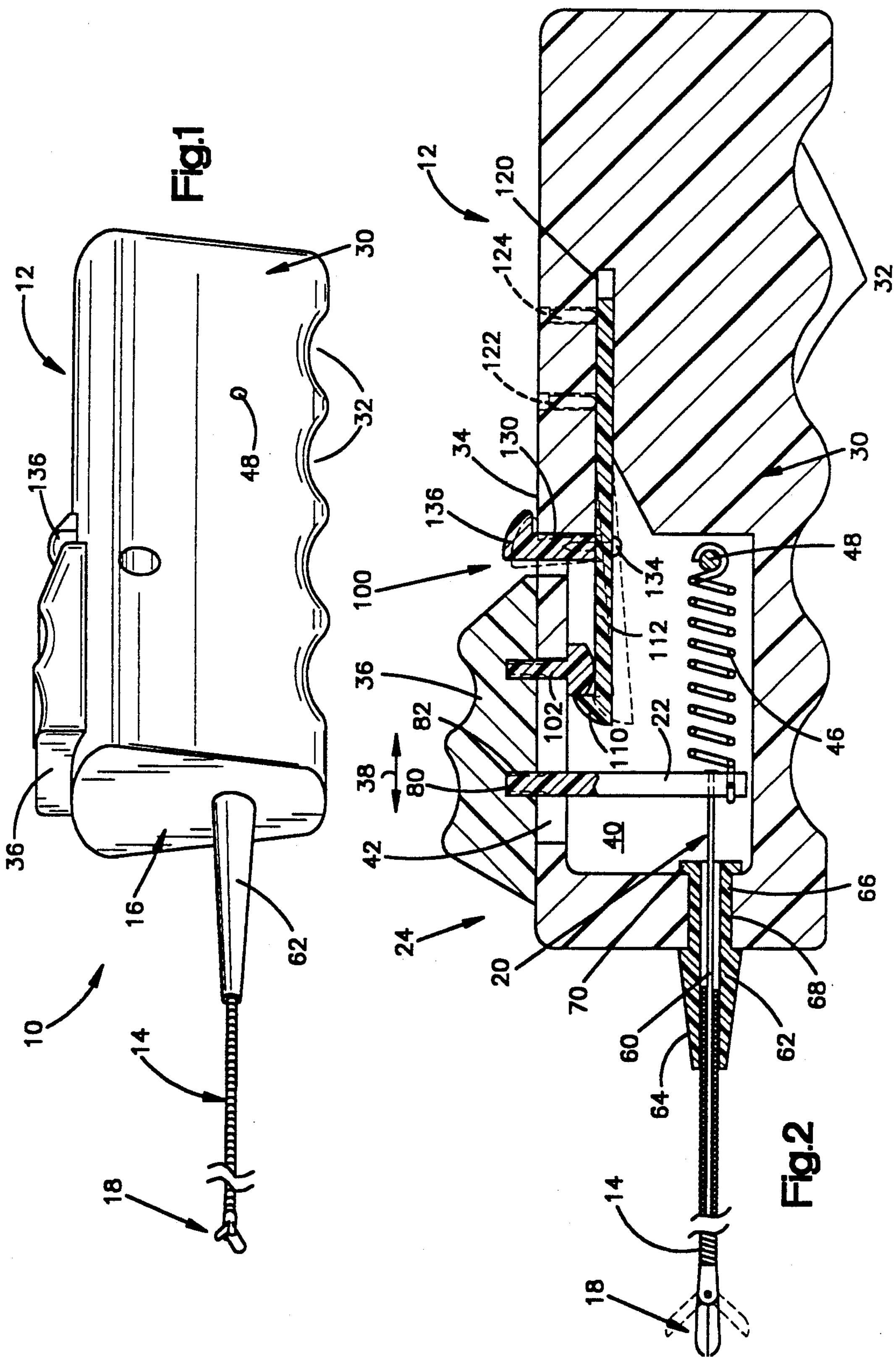
FIG. 1 is a perspective view of a biopsy forceps device constructed in accordance with the present invention.
FIG. 2 is a sectional view of the device illustrated in FIG. 1.

Reference is now made to the drawings wherein the showings are for purposes of illustrating a preferred embodiment only and not for purposes of limiting same. As shown in the drawings, there is provided a biopsy forceps device 10 which includes a handle assembly 12 and an elongated flexible hollow body taking the form of a coil spring guide 14 which extends from the distal end 16 of the handle assembly to a forceps assembly 18. The guide 14 has a lumen extending throughout its length and the lumen slidably receives a control wire 20 which is connected at its distal end to the forceps assembly 18 and a its proximal end extends into the handle assembly and is secured to a transmission shaft 22. The transmission shaft 22 forms a portion of the trigger assembly 24 which is slidably carried by the handle assembly 12.

The handle assembly 12, as best shown in FIG. 2, includes a sword-style handle 30 having finger receiving grooves 32 on its underside (as viewed in FIG. 2). This handle 30 may be grasped by either hand of a physician with four fingers being received in the finger grooves 32 and the thumb being placed on the upper surface 34 of the handle up against a thumb button 36 forming a portion of the trigger assembly 24. The thumb button 36 is coupled to the transmission shaft 22 for slidable movement therewith relative to the handle in the opposing directions indicated by the arrows 38 (FIG. 2).

As best shown in FIG. 2, the handle 30 has a hollowed out portion or cavity 40 within the handle and this hollowed out portion serves to receive the components making up the trigger assembly 24 as well as the lock release mechanism to be described hereinafter. The upper wall of the handle is provided with an elongated slot 42 permitting slidable movement of the transmission shaft 22 in the directions as indicated by the arrows 38 between a rearward position (as shown in FIG. 2) and a forward position (to the left in FIG. 2). This slidable movement of the transmission shaft 22 is caused by displacing the thumb button 36 from its normal rearward position to its forward position by pressure exerted by the operator's thumb. This causes the control wire to be moved in a forward direction to open the forceps 18 permitting the physician to obtain a tissue sample. The transmission shaft 22 is resiliently biased toward its rearward position by means of a coiled spring 46 connected at one end to the transmission shaft and connected at its other end, as by means of a pin 48, to the handle 30 (see FIGS. 1 and 2). Consequently, once the physician has moved the thumb button 36 forward against the resilient bias exerted by spring 46 to open the forceps to obtain a sample, the operator need only remove his thumb from the thumb button and the transmission shaft will return to its rearward position causing the forceps to close trapping the tissue sample in place.

The control wire extends in a forward direction toward the forceps assembly from the transmission shaft 22 through a portion of the open space provided by cavity 40 and thence through a lumen 60 extending through a control wire retainer 62, constructed of plastic material. This retainer 62 includes a nose portion 64 which is tapered inwardly from the handle in the direction toward the forceps device and serves to receive a portion of the length of the coil spring guide 14. In the opposite direction, the retainer has a cylindrical neck portion 66 which extends through a passageway 68 in the front end of the handle and is prevented from dislodgement therefrom by means of a collar 70 located within the cavity 40 in the handle 30.

Figure 3:
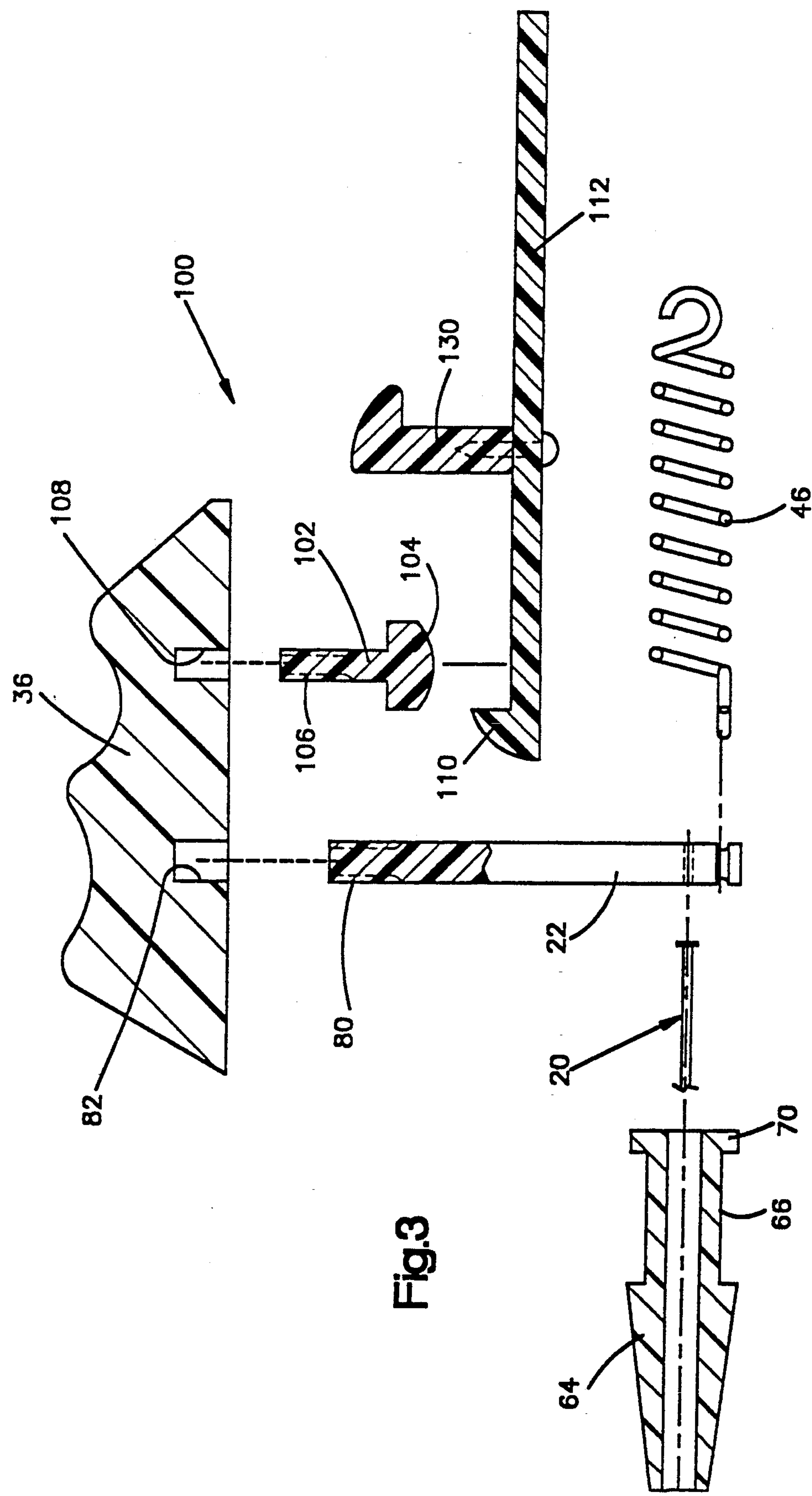
FIG. 3 is an enlarged exploded view showing various of the components employed in the embodiment illustrated in FIGS. 1 and 2.

The proximal end of the control wire 20 is suitably secured to the transmission shaft 22, as by a set pin or screw arrangement (not shown). The transmission shaft 22 is secured to the bottom of the thumb button 36, as by a threaded interconnection. Thus, the upper end of the transmission shaft 22 has a threaded portion 80 which is threaded into a threaded recess 82 which extends into the lower side of the thumb button 36 (see FIG. 3).

The thumb button and transmission shaft are normally held in the rear position, as is shown in FIG. 2, and hence, the forceps assembly 18 is normally in its closed position due to the provision of a releasable locking mechanism 100 (see FIGS. 2 and 3) to be described hereinbelow. This locking mechanism normally prevents forward movement of the thumb button 36 and, hence, of the transmission shaft 22 until the locking mechanism 100 has been released. This locking mechanism includes a stop 102 mounted to the lower surface of the thumb button 36. This stop 102 includes a head 104 and a threaded shaft 106 with the shaft 106 being threadedly received in a threaded aperture 108 in the bottom of the thumb button 36. The head 102 is normally displaced downwardly from the thumb button so that it is blocked from movement in the forward direction by a locking pawl 110. The locking pawl 110 extends upwardly from the free end of a spring arm 112 which is cantilevered from a fixed end. The fixed end is received within a slot 120 in the handle 30 so that the arm 112 is cantilevered therefrom into the cavity 40 within the handle. The fixed end of the spring arm 112 is held in place by means of a pair of set screws 122 and 124 extending downwardly from the upper surface of the handle so as to engage and hold the fixed end of the spring arm in place. A release element 130 extends upwardly from spring arm 112 rearwardly of the thumb button 36 and is held in place at its lower end as by means of a screw 134 extending through the arm 112 and, thence, into the release element 130. The upper end of the release element 130 serves as a release actuator 136.

When the thumb button 36 is in the position, as shown in FIG. 2, the forceps are locked in their closed position because the pawl 112 blocks movement of stop 102 in the forward direction and, hence, prevents movement of the thumb button 36 in the forward direction to open the forceps assembly 18. The lock release mechanism 100 permits such movement by the operator placing his thumb on the release actuator 136 and pressing downwardly, causing the spring arm 112 to flex downwardly to move the pawl 110 out of its blocking relationship with respect to the stop 102. At the same time, the operator presses his thumb in a forward direction causing the thumb button to move in a forward direction resulting in forward movement of the transmission shaft 22. This causes the biopsy forceps to move to its open condition to obtain a tissue sample. When the operator removes his thumb from the thumb button 36, the button 36 will be returned to its normal rearward position by means of the spring 46 causing the pawl 112 to again lock the thumb button in place in its rearward position with the forceps in a closed condition.

Although the invention has been described in conjunction with a preferred embodiment, it is to be appreciated that various modifications may be made without departing from the spirit and scope of the invention as defined by the appended claims.

Having described the invention, the following is claimed:

1. A biopsy forceps device comprising:

a handle;

an elongated flexible hollow body portion having a lumen extending therethrough and having a proximal end and a distal end;

a forceps assembly coupled to the distal end of said body portion, and including a pair of forceps;

control wire means having proximal and distal ends and extending through the lumen in said body portion and coupled at its said proximal end to said handle and at its said distal end to said forceps assembly;

trigger means connected to the proximal end of said control wire means, said trigger means being slidably mounted to said handle for slidable movement relative thereto between a rear position and a forward position for respectively causing said forceps to be in a closed condition and in an open condition;

releasable forceps locking means for normally blocking forward slidable movement of said trigger means when said trigger means is in its said rear position thereby preventing said forceps from being actuated to said open condition; and release means for releasing said locking means from blocking forward movement of said trigger means to thereby permit the forward movement of said trigger means to cause said forceps to be actuated to said open condition.

2. A biopsy forceps device as set forth in claim 1 wherein said locking means includes means for normally blocking forward movement of said trigger means.

3. A biopsy forceps device as set forth in claim 2 wherein said trigger means includes a thumb actuatable button slidably mounted to said handle and which may be actuated by an operator's thumb from a normal rear position to a forward position for causing said forceps assembly to be in its open position.

4. A biopsy forceps device as set forth in claim 3 including means for resiliently biasing said trigger means toward said normal rear position.

5. A biopsy forceps device as set forth in claim 4, wherein said biasing means include an elongated coiled spring interposed between said trigger means and said handle.

6. A biopsy forceps device as set forth in claim 1 wherein said release means includes means for transversely displacing said locking means relative to the direction of said slidable movement so as to thereby unblock said blocking means from preventing forward movement of said trigger means.

7. A biopsy forceps device as set forth in claim 6 wherein said release means includes an elongated spring arm having a free end and an opposing fixed end secured to said handle, a locking pawl carried by said free end of said spring arm for normally blocking forward movement of said trigger means.

8. A biopsy forceps device as set forth in claim 7 wherein said release means includes a thumb operable actuator carried by said spring arm and which may be actuated to displace said locking pawl to unblock forward movement of said trigger means.

* * * * *